United States Patent
Forman et al.

(10) Patent No.: US 6,390,967 B1
(45) Date of Patent: May 21, 2002

(54) RADIATION FOR INHIBITING HYPERPLASIA AFTER INTRAVASCULAR INTERVENTION

(75) Inventors: Michael R. Forman, Vadnais Heights, MN (US); Paul A. Lovoi, Saratoga, CA (US); Tom W. Rusch, Hopkins, MN (US)

(73) Assignee: XOFT microTube, Inc., Fremont, CA (US)

( * ) Notice: Subject to any disclaimer, the term of this patent is extended or adjusted under 35 U.S.C. 154(b) by 0 days.

(21) Appl. No.: 09/661,438

(22) Filed: Sep. 14, 2000

(51) Int. Cl.⁷ .................................................. A61N 5/00
(52) U.S. Cl. ............................................. 600/3; 600/5
(58) Field of Search ..................... 600/3, 7, 1; 604/104, 604/501, 21; 606/40, 198; 378/122

(56) References Cited

U.S. PATENT DOCUMENTS

| | | | |
|---|---|---|---|
| 5,059,166 A | 10/1991 | Fischell et al. ............... 600/3 |
| 5,061,267 A | 10/1991 | Zeiher ......................... 606/40 |
| 5,199,939 A | 4/1993 | Dake et al. ................... 600/3 |
| 5,213,561 A | 5/1993 | Weinstein et al. ............. 600/7 |
| 5,256,141 A | 10/1993 | Gencheff et al. ............. 604/53 |
| 5,302,168 A | 4/1994 | Hess ............................. 600/3 |
| 5,354,257 A | 10/1994 | Roubin et al. ................ 600/7 |
| 5,411,466 A | 5/1995 | Hess ............................. 600/3 |
| 5,484,384 A | 1/1996 | Fearnot ........................ 600/3 |
| 5,498,227 A | 3/1996 | Mawad ........................ 600/3 |
| 5,503,613 A | 4/1996 | Weinberger ................... 600/3 |
| 5,540,659 A | 7/1996 | Teirstein ..................... 604/104 |
| 5,616,114 A | 4/1997 | Thorton et al. ............... 600/3 |
| 5,618,266 A | 4/1997 | Liprie ......................... 604/21 |
| 5,624,372 A | 4/1997 | Liprie ......................... 600/3 |
| 5,643,171 A | 7/1997 | Bradshaw et al. ............ 600/1 |
| 5,653,736 A | 8/1997 | Glastra ...................... 606/198 |
| 5,713,828 A | * 2/1998 | Coniglione .................... 600/7 |
| 5,971,909 A | 10/1999 | Bradshaw et al. ............ 600/3 |
| 6,059,713 A | * 5/2000 | Urick et al. .................. 600/3 |
| 6,069,938 A | 5/2000 | Chornenky et al. ......... 378/122 |
| 6,108,402 A | 8/2000 | Chornenky et al. ......... 378/119 |
| 6,159,141 A | * 12/2000 | Apple et al. .................. 600/3 |

FOREIGN PATENT DOCUMENTS

| | | |
|---|---|---|
| EP | 688 580 | 12/1995 |
| EP | 593 136 | 3/1997 |
| EP | 860 180 | 8/1998 |
| EP | 633 041 | 9/1999 |
| WO | WO 96/13303 | 5/1996 |
| WO | WO 96/14898 | 5/1996 |
| WO | WO 97/07740 | 3/1997 |

* cited by examiner

*Primary Examiner*—Eric F. Winakur
(74) *Attorney, Agent, or Firm*—Townsend and Townsend and Crew LLP

(57) ABSTRACT

Apparatus and methods are provided for applying a radially uniform radiation dose to an intravascular treatment region to inhibit hyperplanes, and specifically to reduce "candy-wrapper" ends, following intravascular intervention. An embodiment of the apparatus comprises a catheter body having a proximal end and a distal end, a pair of axially spaced apart radiation shields on the catheter body, and a radiation source. The radiation source applies a radiation dose which is substantially uniform in a radial direction over an entire distance between the axially spaced apart shields.

25 Claims, 8 Drawing Sheets

RADIATION FOR INHIBITING HYPERPLASIA AFTER INTRAVASCULAR INTERVENTION

BACKGROUND OF THE INVENTION

1. Field of Invention

The present invention relates generally to apparatus and methods for inhibiting restenosis in a blood vessel after an initial treatment for opening a stenotic region in the blood vessel. More particularly, the present invention relates to radiation treatment for inhibiting hyperplasia following balloon angioplasty and other intravascular interventional treatments.

Percutaneous translumenal angioplasty (PTA) procedures are widely used for treating stenotic atherosclerotic regions of a patient's vasculature to restore adequate blood flow. The catheter, having an expansible distal end usually in the form of an inflatable balloon, is positioned in the blood vessel at the stenotic site. The expansible end is expanded to dilate the vessel to restore adequate blood flow beyond the diseased region.

While PTA has gained wide acceptance, it continues to be limited by the frequent occurrence of restenosis. Restenosis afflicts approximately up to 50% of all angioplasty patients and is the result of injury to the blood vessel wall during the lumen opening angioplasty procedure. In some patients, the injury initiates a repair response that is characterized by smooth muscle cell proliferation referred to as hyperplasia in the region traumatized by the angioplasty. The hyperplasia of smooth muscle cells narrows the lumen that was opened by the angioplasty, thereby necessitating a repeat PTA or other procedure to alleviate the restenosis.

Many different strategies have been proposed to reduce the restenosis rate resulting from hyperplasia, including mechanical (e.g., prolonged balloon inflations during angioplasty, stenting, and the like), pharmacological, (e.g., the administration of anti-proliferative drugs following angioplasty), and other experimental procedures, all of which have had limited success.

As an alternative to mechanical devices and pharmacological drug delivery, use of intravascular radiotherapy (IRT) for the inhibition of hyperplasia following PTA has been proposed and is currently being commercialized. It has also been speculated that IRT may be used to prevent hyperplasia following cardiovascular graft procedures or other trauma to the vessel wall. Proper control of the radiation dosage is critical to impair or arrest hyperplasia without causing excessive damage to healthy tissue. Overdosing of a section of a blood vessel can cause arterial necrosis, inflammation, and hemorrhaging. Underdosing will result in no inhibition of smooth muscle cell proliferation, or even exacerbation of the hyperplasia and resulting restenosis.

A variety of catheters, guidewires, and stents have been configured for positioning a radioactive source within a blood vessel after angioplasty and other intravascular interventional treatments. In most cases, the devices have been configured to position a solid radioactive source, such as a wire, strip, pellet, or the like, within the blood vessel. It has also been proposed to deliver liquid radioactive medium to inflate a balloon catheter within the blood vessel. In the latter case, the balloon has been specially configured to prevent leakage of the radioactive material from the balloon into the blood vessel or blood stream. Of particular interest to the present invention, it has been proposed to use x-ray sources at the distal end of a catheter. The x-ray source permits convenient dosing where the source may be easily turned on and off and eliminates the need to prepare, handle, and dispose of radioisotopes.

While holding great promise, the use of radiation dosing to inhibit hyperplasia in blood vessels has not been entirely successful. In particular, hyperplasia will often still occur starting at the proximal and distal edges of an IRT treated blood vessel region and extending out 3 mm to 5 mm, producing so called "candy-wrapper" ends, as illustrated in FIG. 1. It is speculated that non-uniform dose distribution at the proximal and distal edges of IRT catheters or stents is the most likely cause of this "candy-wrapper" effect. In particular, it is suggested that this high rate of cell growth at the ends is due to an interaction that occurs between blood vessel tissue beyond the IRT catheter or stent edges and a low radiation dose that results from a dose fall off on the edges. Radiation dose fall off at the ends, as shown in FIG. 2, results from the fact that the total radiation experienced by any point along the length of a blood vessel will depend on the amount and distance of all radioisotope sources on either side of it. For that reason, those points near the end of the length will necessarily receive less total radiation (i.e., from all points along the treatment region) than those near the middle. As such, use of current IRT catheters or stents is problematic since it can be difficult to provide delivery of a uniform radioactive dose throughout the blood vessel wall to prevent "candy-wrapper" ends.

Approaches to solving this "candy-wrapper" effect are currently under investigation. Primary studies have proposed increasing the dose of radiation at the edge to push the low dose exposure to an area beyond the region of injury to the vessel wall. Although irradiating beyond the region of injury appears to be working, the major drawback of this approach is that a majority of the vessel wall ends up being irradiated, including a considerable amount of non-damaged tissue. Further, as it is believed that a vessel can not be irradiated twice since dose is cumulative, future treatment problems may arise if restenosis occurs later in already irradiated tissue. Implanting a stent with a lower activity radioisotope in the middle and higher activity radioisotopes on the ends has also been suggested. However, this approach still suffers from radiation dose fall off on tissue which are close to the blood vessel and which encourage proliferative cell growth.

For these reasons, it would be desirable to provide improved devices and methods for inhibiting restenosis and hyperplasia following angioplasty and other intravascular interventional treatments. In particular, it would be desirable to provide improved apparatus, methods, and the like, for delivering radiation dosages to the blood vessel which are sufficiently uniform to prevent hyperplasia without encountering the "candy-wrapper" effect. Preferably, the improved devices and methods will be useful with all presently known modalities for delivering IRT to blood vessels including wire sources, pellet sources, liquid sources, x-ray sources, and the like. At least some of these objectives will be met by the present invention.

2. Description of the Background Art

Devices and methods for exposing intravascular and other treatment locations to radioactive materials are described in the following: U.S. Pat. Nos. 6,069,938; 5,971,909; 5,653,736; 5,643,171; 5,624,372; 5,618,266; 5,616,114; 5,540,659; 5,503,613; 5,498,227; 5,484,384; 5,411,466; 5,354,257; 5,302,168; 5,256,141; 5,213,561; 5,199,939; 5,061,267; and 5,059,166, European applications 860 180; 688 580; 633 041; and 593 136, and International Publications WO 97/07740; WO 96/14898; and WO 96/13303.

SUMMARY OF THE INVENTION

The present invention provides apparatus and methods for inhibiting hyperplasia in blood vessels after intravascular intervention. In particular, the methods can inhibit hyperplasia while reducing or eliminating the proliferative end effect, commonly called the "candy-wrapper" effect, which often accompanies such treatment.

The term "hyperplasia" refers to the excessive growth of the vascular smooth muscle cells which can result from an injury to the blood vessel wall resulting from angioplasty or other intravascular interventional procedures. The term "candy-wrapper" ends refers to a particular type of hyperplasia that often still occurs even in a radiotherapy treated blood vessel. As shown in FIG. 1, such "candy-wrapper" ends typically start at the proximal and distal edges of a treatment region and extend out 3 mm to 5 mm or more. "Candy-wrapper" ends may result from a non-uniform radiation dose on the ends of a radiotherapy catheter or stent (see FIG. 2). Such proliferative cell growth can result in restenosis of the blood vessel lumen that was previously opened by the angioplasty even when the radiation therapy successfully inhibits hyperplasia in the center portion of the treatment region. By inhibiting hyperplasia, especially "candy-wrapper" ends, the present invention can eliminate the need for subsequent angioplasty, atherectomy, bypass, and other procedures intended to restore blood perfusion.

The term "intravascular intervention" includes a variety of corrective procedures that may be performed to at least partially resolve a stenotic condition. The blood vessel may be any blood vessel in the patient's vasculature, including veins, arteries, and particularly including coronary arteries, and prior to performing the initial corrective procedure, the blood vessel could have been partially or totally occluded at the target site. Usually, the corrective procedure will comprise balloon angioplasty, atherectomy, rotational atherectomy, laser angioplasty, or the like, where the lumen of the treated blood vessel is enlarged to at least partially alleviate a stenotic condition which existed prior to the treatment. The corrective procedure could also involve coronary artery bypass, vascular graft implantation, endarterectomy, or the like. Of particular interest to the present invention, the corrective procedure may additionally include procedures for controlling restenosis, such as stent placement which provides for vascular remodeling but which often does not successfully inhibit neointimal hyperplasia.

According to the present invention, a radiation delivery catheter may comprise a catheter body having a proximal end and a distal end, a pair of axially spaced apart radiation shields on the catheter body, and a radiation source. After intravascular intervention, the radiation delivery catheter is introduced percutaneously to the patient's vasculature and advanced within the patient's blood vessel so that the shields are positioned on either end of a treatment region. The "treatment region" will be a length within the blood vessel which is at risk of hyperplasia, typically as a result of the initial intravascular intervention(s). A radiation dose is then applied between the first and second shields so that the radiation dose directed at tissue outside of the shields is attenuated sufficiently to inhibit hyperplasia outside of the shields. Preferably, the radiation dose is radially uniform. In order to reduce the risk of hyperplasia in the treatment region between the shields, it is important to apply the radiation dose uniformly out substantially the entire distance between the spaced apart shields. In this way, the radiation can have a generally uniform dosage over the entire distance between the shields (which will preferably cover the entire region at risk of hyperplasia) while a very sharp cut off will be provided at each end of the dosed region, as defined by the shields. The sharp cut off resulting from uniform dosimetry, as seen in FIG. 3, greatly reduces the risk of "candy-wrapper" ends.

The radiation shields may be permanently affixed to an outer surface of the catheter and may comprise elastomeric balloons that are filled, preferably with a non-toxic radiopaque contrast medium. The radiation shields may alternatively comprise spiral perfusion radiation balloons which allow for both perfusion and radiation blocking. Radiation shields may also be used to center and correctly position the radiation source within the blood vessel. In an exemplary embodiment, the radiation source is translated axially relative to the catheter so that the radiation source can travel between the shields to apply the uniform radiation dose. The radiation source is preferably an x-ray tube since it provides many advantages, such as being easily turned on and off, minimal disposal problems, and the like. The catheter of the present invention may also be equipped with perfusion ports proximal and distal the radiation shields to permit blood flow past the shields/balloons when inflated.

According to another embodiment of the present invention, the radiation source is a fixed source, such as a wire or liquid radioisotope filled balloon, that is immobilized on the catheter. The radiation shields are positioned immediately adjacent to each end of the fixed radioisotope source so as to inhibit hyperplasia effects at distal and proximal ends of a treatment region. The radioisotopic liquid may be selected to emit alpha, beta, or gamma radiation. Usually, alpha and beta radiation are preferred since they may be quickly absorbed by surrounding tissue and will not penetrate substantially beyond the wall of the blood vessel being treated. Accordingly, incidental irradiation of the heart and other organs adjacent to the treatment region can be substantially eliminated.

According to another embodiment of the present invention, the radiation source is a receptacle in the catheter body for receiving radioisotopic materials like pellets or liquids. In such cases, the catheter will usually include a radioisotopic inflation lumen to permit delivery and removal of the radioisotopic materials to the receptacle.

Another aspect of the present invention is a method for applying a radiation dose to a body lumen. The method includes positioning a first radiation shield at a first location in the body lumen. A second radiation shield is positioned at a second location spaced apart from the first location in the body lumen. A radially uniform radiation dose is applied between the first and second shields, so that the radiation dose directed at tissue outside of the shields is attenuated sufficiently to inhibit hyperplasia outside of the shields.

DESCRIPTION OF THE SPECIFIC EMBODIMENTS

Figure 1:
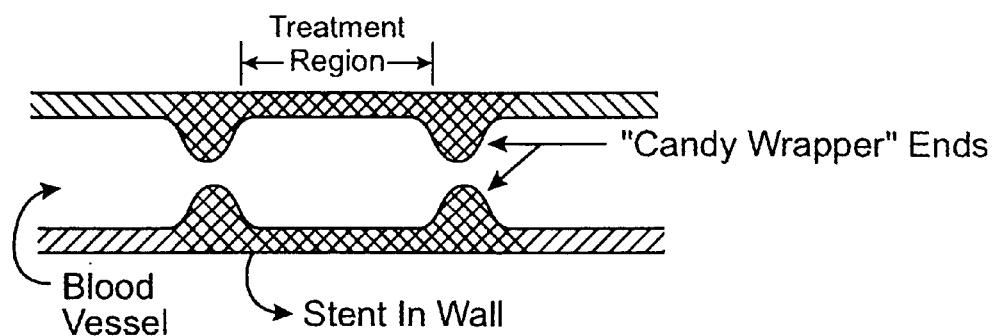
FIG. 1 is a cross sectional view of a vessel wall exhibiting "candy-wrapper" effects after intravascular intervention.
Figure 2:
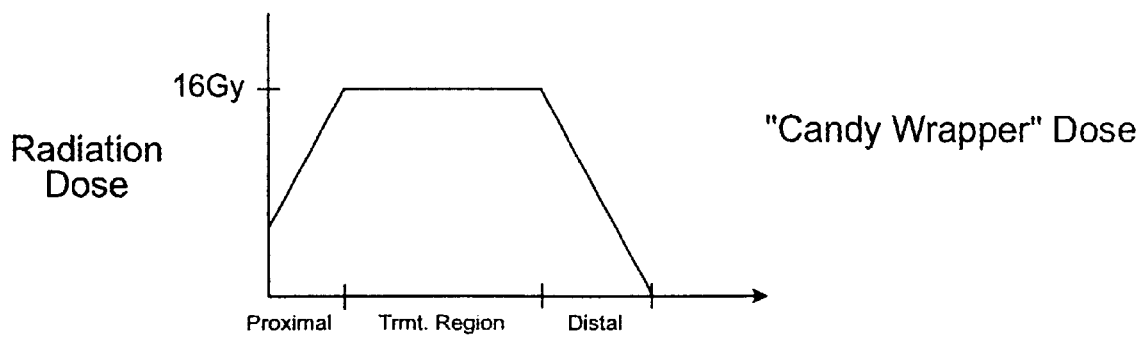
FIG. 2 is a graphical representation modeling the cause of "candy-wrapper" effects.
Figure 3:
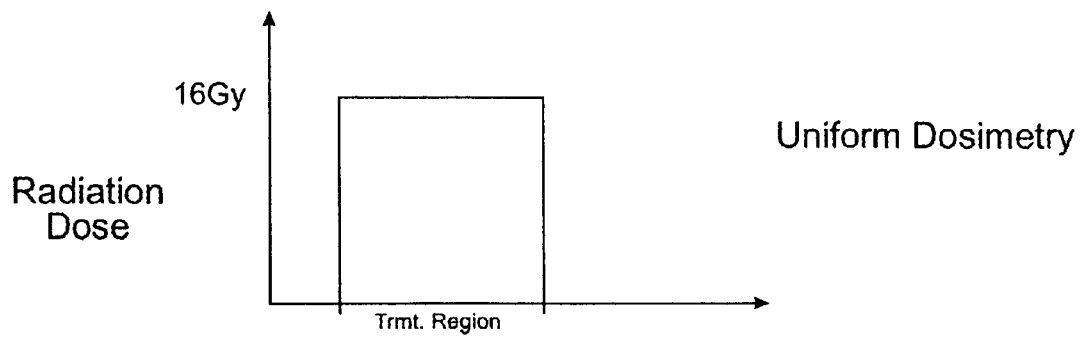
FIG. 3 is a graphical representation of uniform dosimetry.
Figure 4A:
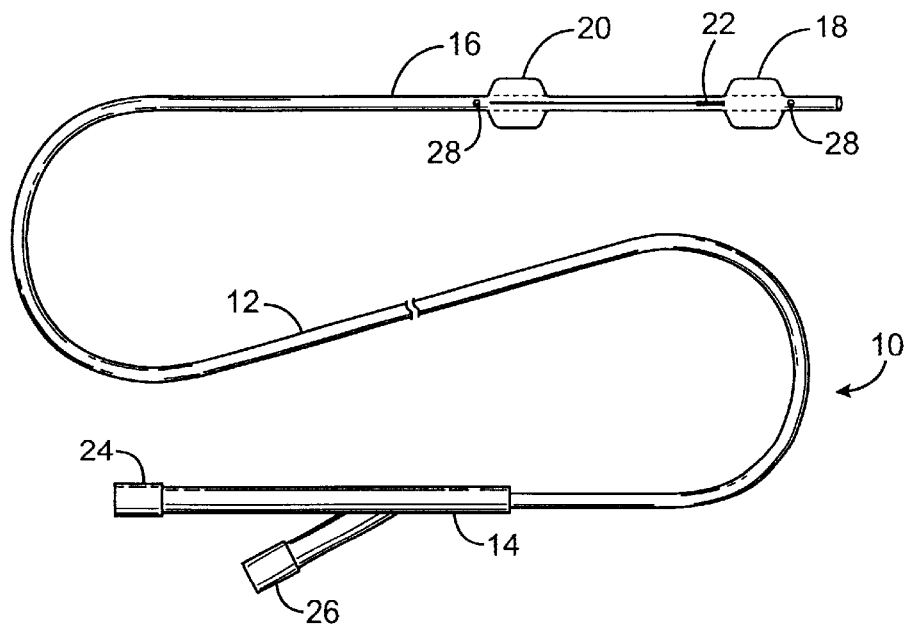
FIGS. 4A and 4B are plan and cross sectional views of an apparatus according to the present invention.
Figure 4B:
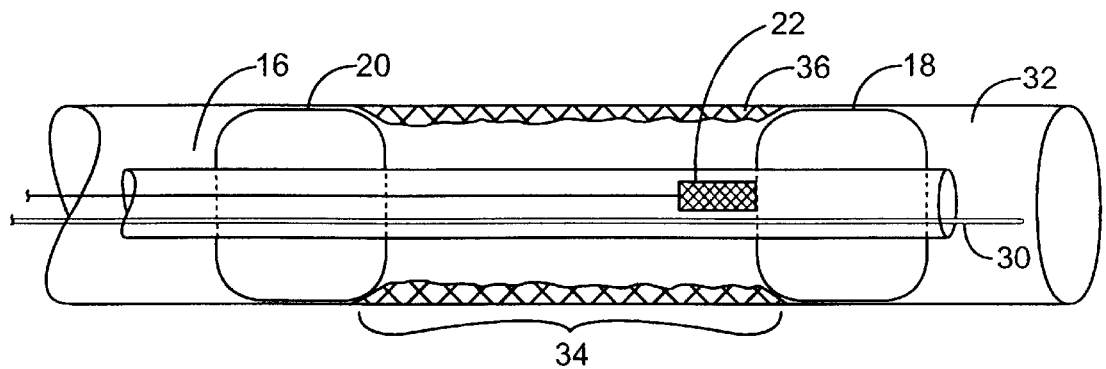

The devices and methods of the present invention rely on the delivery of a uniform radiation dose to an intravascular treatment region to inhibit hyperplasia, and specifically to reduce "candy-wrapper" ends, following intravascular intervention. FIGS. 4A and 4B illustrate an intravascular radiation delivery catheter 10 according to the present invention. The radiation delivery catheter 10 comprises a shaft 12 having a proximal end 14 and a distal end 16 and a pair of axially spaced apart radiation shields 18 and 20 with a radiation source 22 located therebetween on the distal end 16 of shaft 12. The proximal end 24 of shaft 12 includes a guidewire lumen luer fitting 24 and a radiation shield luer fitting 26. The guidewire lumen luer fitting 24 is in fluid communication with a guidewire/perfusion/infusion/aspiration lumen, through which drugs may be infused or aspirated directly into the patient's blood stream. The radiation shield luer fitting 26 is in fluid communication with a radiation shield inflation lumen that is in turn in fluid communication with radiation shields 18 and 20 via radiation shield inflation ports.

Radiation shields 18 and 20 are immediately adjacent to and between perfusion ports 28, which are in fluid communication with the guidewire lumen. Perfusion ports 28 are well known in the art as a means of permitting some blood flow past a shield/balloon that is inflated within and otherwise blocking a blood vessel.

FIG. 4B is an enlarged cross sectional view of the distal end 16 of the present embodiment of the catheter 10. FIG. 4B illustrates the apparatus and method for preventing restenosis due to hyperplasia, especially "candy-wrapper" ends, in a blood vessel after intravascular intervention. Specifically, the distal end 16 of shaft 12 is positioned via a guidewire 30 within a blood vessel segment 32 having a treatment region 34. The treatment region 34 has previously been enlarged by balloon angioplasty or other procedures such that atherosclerotic plaque has been radially compressed by expansion of the balloon portion of an angioplasty device (not shown). Additionally, a stent 36 has been positioned against the treatment region 34 on the vessel wall 32 via a stent delivery system (not shown).

Radiation shields 18 and 20 are usually permanently affixed to an outer surface of shaft 12, proximal and distal of a treatment region 34, and between perfusion ports 28 by suitable adhesives, heat welding, or the like. Radiation shields 18 and 20 comprise inelastic or preferably elastic balloons, which are preferably made of polyurethane, Pebax, or other medical grade elastomeric material suitable for constructing puncture-resistant elastic balloons. Preferably, the radiation balloons 18 and 20 are cylindrical and have flattened end(s) at least facing the treatment region 34.

Radiation shields 18 and 20 are generally inflatable with a commonly used non-toxic radiopaque contrast medium. Suitable inflation media includes Hexabrix 320™ (sold commercially by Mallinkrodt Corp.) and Iopamiron ™ (sold commercially by Schering-Plough Corp.). Contrast media with higher concentrations of the radiopaque material (e.g. iodine) are preferred. For ionic contrast, 300 mg/ml and higher is preferred and will block more than 50% of soft x-rays.

Figure 4C:
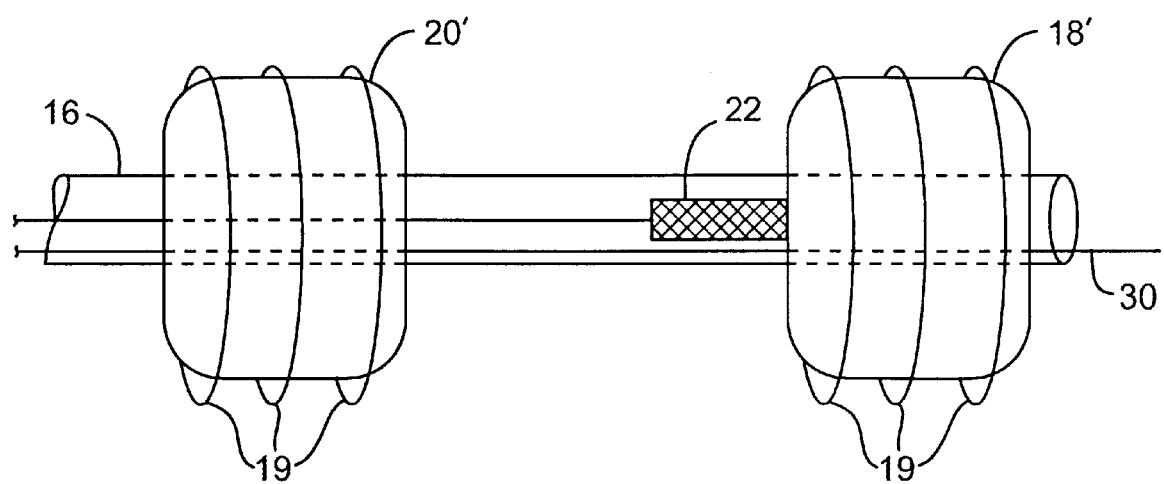
FIG. 4C shows a distal tip of a catheter with spiral perfusion radiation shields.

In some instances, the radiation shields may comprise spiral perfusion radiation balloons 18', 20', as illustrated in FIG. 4C. Spiral perfusion radiation balloons 18', 20' comprise a threading or band 19 affixed to outer surfaces of the radiation balloons by adhesion bonding, heat welding, fasteners, or the like. Threading patterns may be spiral (as shown in FIG. 4C), helical, or angled. The threading 19 may be formed from polymer materials and may aid in perfusion so as to permit blood flow past the balloons when inflated. Spiral threading 19 may also be filled with suitable inflation media to provide additional radiation blocking or shielding.

Although inflatable balloons will generally be preferred for use as the radiation shields 18 and 20, it will also be possible to use other deployable structures, such as radially expansible braids, meshes, malecots, and other mechanically actuated structures. In such cases, the structure should have a thickness sufficient to block the radiation being employed.

The radiation source 22 is positioned between the radiation shields 18 and 20 so that it can either be translated axially or fixed relative to the catheter shaft 12. The radiation source 22 is a radioisotope, a receptacle or lumen for receiving radioisotopic materials. In an exemplary embodiment, the radiation source is an x-ray tube, as illustrated in FIG. 4b. The x-ray tube can be isotropic, such as a transmission anode, or non-isotropic, such as an opaque anode. The x-ray will typically operate at an energy in the range from 10 kV to 30 kV. Suitable x-ray sources are described in copending U.S. application Ser. No. 09/299,304, assigned to the assignee herein. Radioisotope sources can comprise a point source, wire, strip, pellet, liquid radioisotope balloon, or the like. Further, the radiation source 22 in the catheter may comprise a receptacle or lumen that receives radioactive material.

In operation, after intravascular intervention, an appropriately sized catheter 10 according to the present invention is selected and advanced within the patient's blood vessel 32 by conventional means so that the shields 18 and 20 are each positioned on an end of a treatment region 34. Radiation shields 18 and 20 are then inflated in the blood vessel with non-toxic radiopaque contrast medium until the blood flow past the shields is substantially stopped (the flow of blood in the vessel itself continues through the perfusion ports 28). Radiation shields 18 and 20 may also aid in centering a radiation source 22 within the blood vessel lumen as well as act as markers for proper positioning of the distal end 16 of catheter 10 within the treatment region 34 of the blood vessel under fluoroscopy.

The x-ray tube radiation source 22 of FIG. 4B is then turned on and translated axially relative to the catheter shaft 12 so that the x-ray tube radiation source 22 can travel between shields 18 and 20 to apply a substantially uniform radiation dose in the radial direction over an entire distance between the axially spaced apart shields. The radiation shields 18 and 20 sufficiently attenuate radiation from reaching tissue beyond the shields so that radiation dose fall off at the distal and proximal ends of a treatment region are minimized and hyperplasia outside of the shields is inhibited. The x-ray tube radiation source is translated between the radiation shields for a predetermined period of time calculated to deliver an effective uniform dose of radiation to the wall of the blood vessel. The x-ray tube radiation source is then turned off, radiopaque liquid is withdrawn from the radiation shields, and the radiation delivery catheter 10 is removed from the patient's body.

Figure 5A:
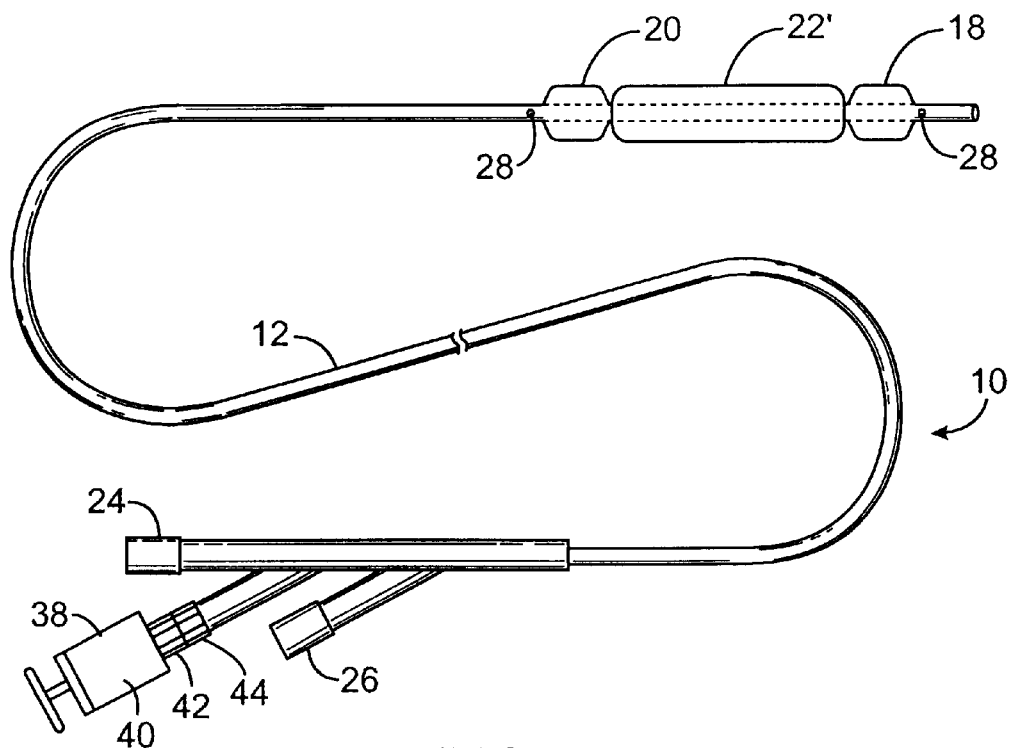
FIGS. 5A and 5B are plan and cross sectional views of an alternate embodiment of an apparatus according to the present invention wherein the radiation source is a fixed liquid radioisotopic filled balloon.
Figure 5B:
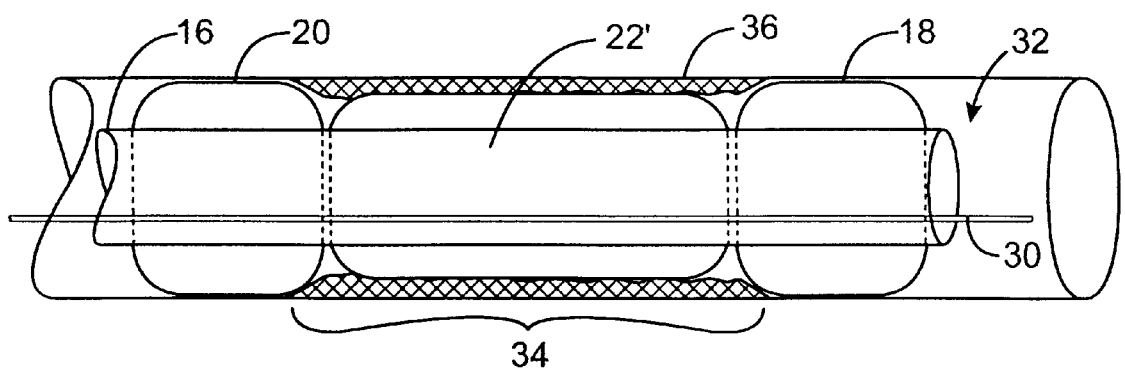

FIGS. 5A and 5B are an alternate embodiment of an apparatus according to the present invention wherein the radiation source is a fixed liquid radioisotopic filled balloon 22'. Radioisotopic balloon 22' is disposed at the distal end 16 of shaft 12 and is immobilized at its proximal and distal ends on the catheter shaft 12. Radiation shields 18 and 20 are positioned immediately adjacent to each end of the fixed radioisotopic balloon 22'. The radioisotopic balloon 22' is an elastic or preferably an inelastic balloon, which may preferably be made from polyethylene terephthalate (PET), polyvinyl chloride (PVC), or other medical grade material suitable for constructing a strong non-compliant balloon.

A shielded injector 38, which may be a manual or automated syringe containing a radioisotopic liquid 40, or a pump connected to a reservoir of radioisotopic liquid 40, is connected to the proximal end of shaft 12. Shielded injector 38 is in fluid communication with a radioisotopic inflation lumen, which in turn is in fluid communication with radioisotopic balloon 22' via radioisotopic inflation lumen ports. To prevent possible spillage and corresponding radioisotopic contamination of the operating room and/or its personnel, the shielded injector 38 is equipped with a fail-safe non-detachable connector 42, which cannot be detached from the corresponding receptacle 44 of shaft 12 once it is attached thereto. Non-detachable connector 42 also prevents the radioisotopic fluid 40 from being discharged from injector 38 until the connector is connected to the receptacle in shaft 12. Connectors having ring-detents and other non-detachable fluid fittings are well known in the art, as are piercing valves and other common methods of preventing fluid flow prior to attachment of a fluid fitting.

In operation, after intravascular intervention, an appropriately sized catheter 10 according to the present invention is selected and advanced within the patient's blood vessel 32 by conventional means so that the shields 18 and 20 are each positioned on an end of a treatment region 34. Radiation shields 18 and 20 are then inflated in the blood vessel with non-toxic radiopaque contrast medium until the blood flow past the shields is substantially stopped (the flow of blood in the vessel itself continues through the perfusion ports 28).

The radioisotopic balloon 22' is then filled with the liquid containing the radioisotope until the outer wall of the radioisotopic balloon 22' gently engages the inner wall of the blood vessel so it can apply a substantially uniform radiation dose in the radial direction over an entire distance between the shields. The radiation shields 18 and 20 sufficiently attenuate radiation from reaching tissue beyond the shields so that radiation dose fall off at the distal and proximal ends of a treatment region are minimized and hyperplasia outside of the shields is inhibited. The radioisotopic balloon 22' is maintained in this inflated state for a predetermined period of time calculated to deliver an effective uniform dose of radiation to the wall of the blood vessel. The radioisotopic liquid is then withdrawn from the radioisotopic balloon 22', the radiopaque liquid is withdrawn from the radiation shields 18 and 20, and the catheter 10 is removed from the patient's body.

For added safety, prior to filling radioisotopic balloon 22' with radioisotopic liquid, radioisotopic balloon 22' may be filled with a commonly used non-toxic radiopaque contrast medium to verify integrity of the radioisotopic balloon 22' via fluoroscopy, pressure, or other suitable means. Once the integrity is verified, the contrast medium would be evacuated and the shielded syringe 38 connected to the receptacle at the proximal end 14 of the catheter shaft 12 would be activated. Although the small amount of contrast medium that would remain in the radioisotopic balloon 22' would dilute the radioisotopic liquid, the amount of dilution would be measurable and could be compensated.

Figure 6A:
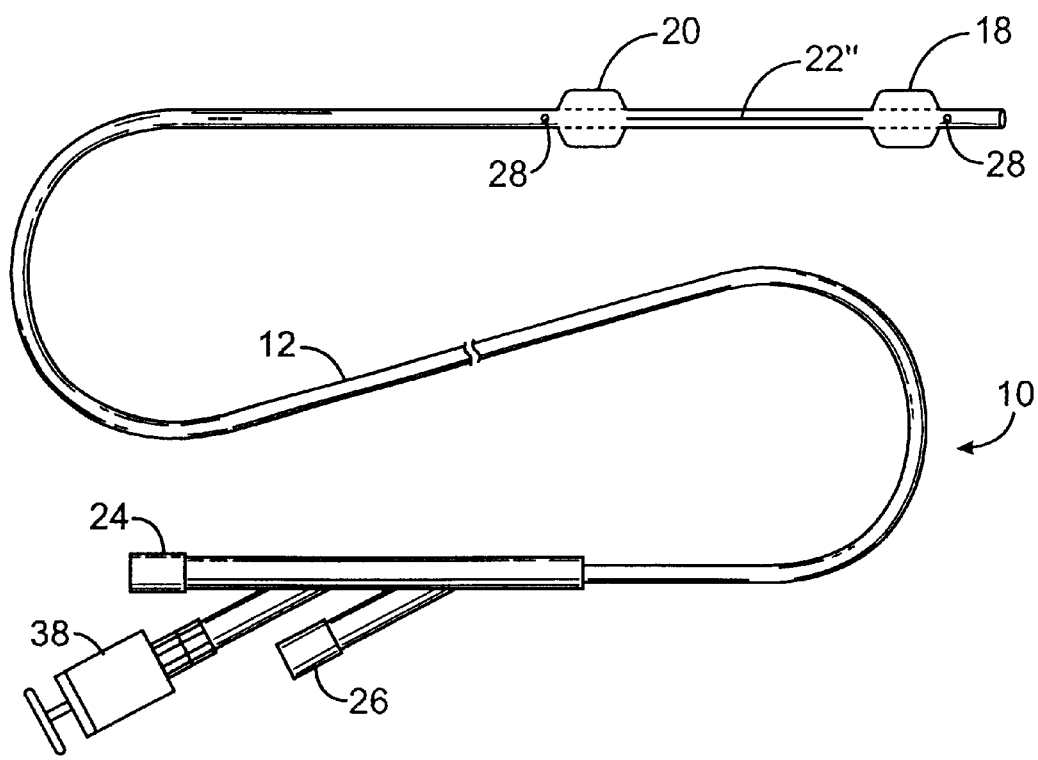
FIGS. 6A and 6B are plan and cross sectional views of an alternate embodiment of an apparatus according to the present invention wherein the radiation source in the catheter is a receptacle.
Figure 6B:
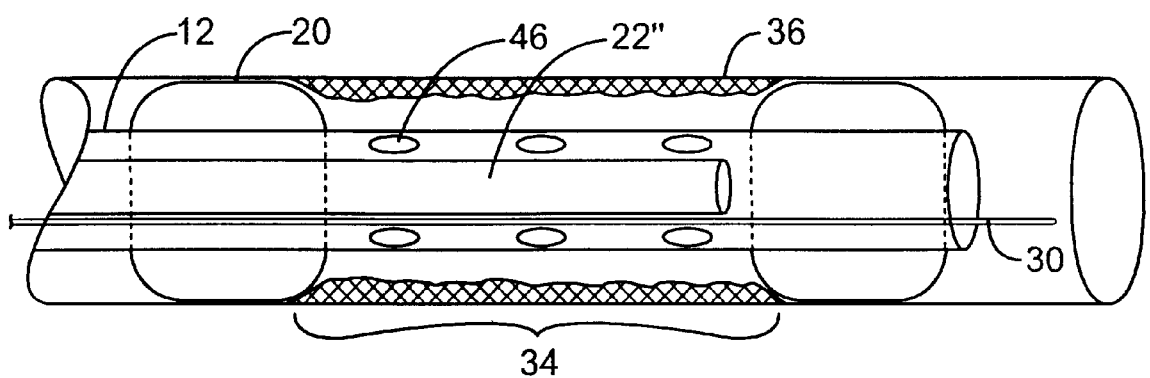

FIGS. 6A and 6B illustrate an additional embodiment of the present invention wherein the radiation source in the catheter is a receptacle or lumen 22" in a catheter shaft 12 for receiving radioisotopic materials, like pellets or liquids, and delivering them through the catheter into the wall of a blood vessel. Receptacle 22" illustrates that the radiation source does not have to be an active source integrated into the catheter, but rather can be a receptacle 22" in the catheter for receiving radioactive material. The catheter will usually include a radioisotopic inflation lumen to permit delivery and removal of the radioisotopic materials to the receptacle 22". Infusion or aspiration ports 46 may also be located between the shields 18 and 20. Infusion ports 46 are in fluid communication with the guidewire/infusion/aspiration lumen to infuse drug's directly into the patient's blood stream.

Several important considerations must be balanced in the design of an apparatus for safely and effectively injecting a radioisotopic material into a patient to irradiate a blood vessel to prevent hyperplasia. Radioisotopic materials may be selected to emit alpha, beta, or gamma radiation. The preferred liquid radioisotopic material will have relatively short half-lives. A shorter half-life is preferred because in the event of a catastrophic failure involving leakage of radioisotopic material into the patient's blood stream, for a given calculated dose, a shorter half life can result in a lesser total body dosage. Radioisotopic material will be selected to provide a total radiation dose in the range from 1 Gray (Gy; 1 Gy=100 rads) to 40 Gy. Suitable emitters of low penetrating radiation for use according the present invention include 90 Strontium, with an initial activity in the range from 20 milliCurie (mCi) to 50 mCi, 90 Yttrium, with an initial activity in the range from 20 mCi to 50 mCi, 32 Phosphorus, with an initial activity in the range from 20 mCi to 50 mCi, 125 Iodine, with an initial activity in the range from 1 Ci to 3 Ci, 103 Palladium, with an initial activity in the range from 1 Ci to 3 Ci. These emitters may be incorporated into or delivered in a solid, liquid, or gaseous form.

Figure 7A:
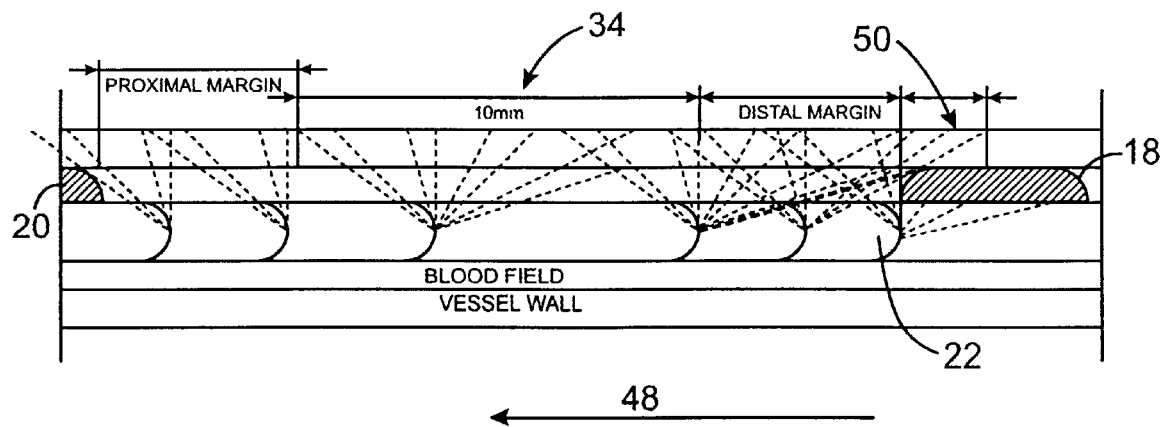
FIGS. 7A and 7B are cross sectional views of a translating radiation source according to an apparatus as modeled in FIG. 4B and an apparatus with no radiation shields.
Figure 7B:
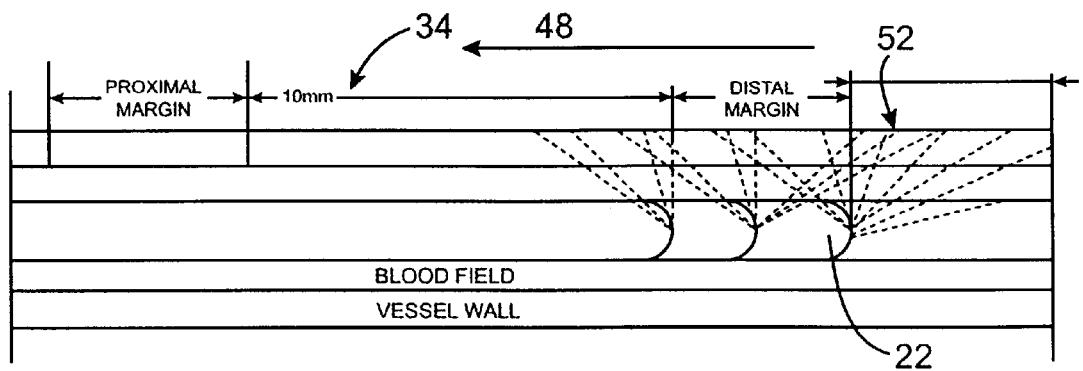

FIGS. 7A and 7B illustrate cross sectional views of a translating radiation source according to an exemplary embodiment as modeled in FIG. 4B and an apparatus with no radiation shields. The direction of the radiation source translation is depicted by arrow 48. In this example, the treatment region 34 is about 10 mm with a proximal and distal margin of about 5 mm each. In FIG. 7A, as the x-ray tube radiation source 22 is translated in direction 48, radiation shield 18 sufficiently attenuates the x-rays from striking and penetrating the tissue outside of the shield. This in turn minimizes hyperplasia outside of the shields since a substantially uniform radiation dose between the shields is applied. The area of radiation dose fall off 50 is approximately 2.2 mm from a distal end of the distal margin. In contrast, FIG. 7B illustrates that a radiation source 22 without any radiation shields exhibits an increased radiation dose fall off 52 of approximately 5 mm from the distal end of the distal margin.

Figure 8:
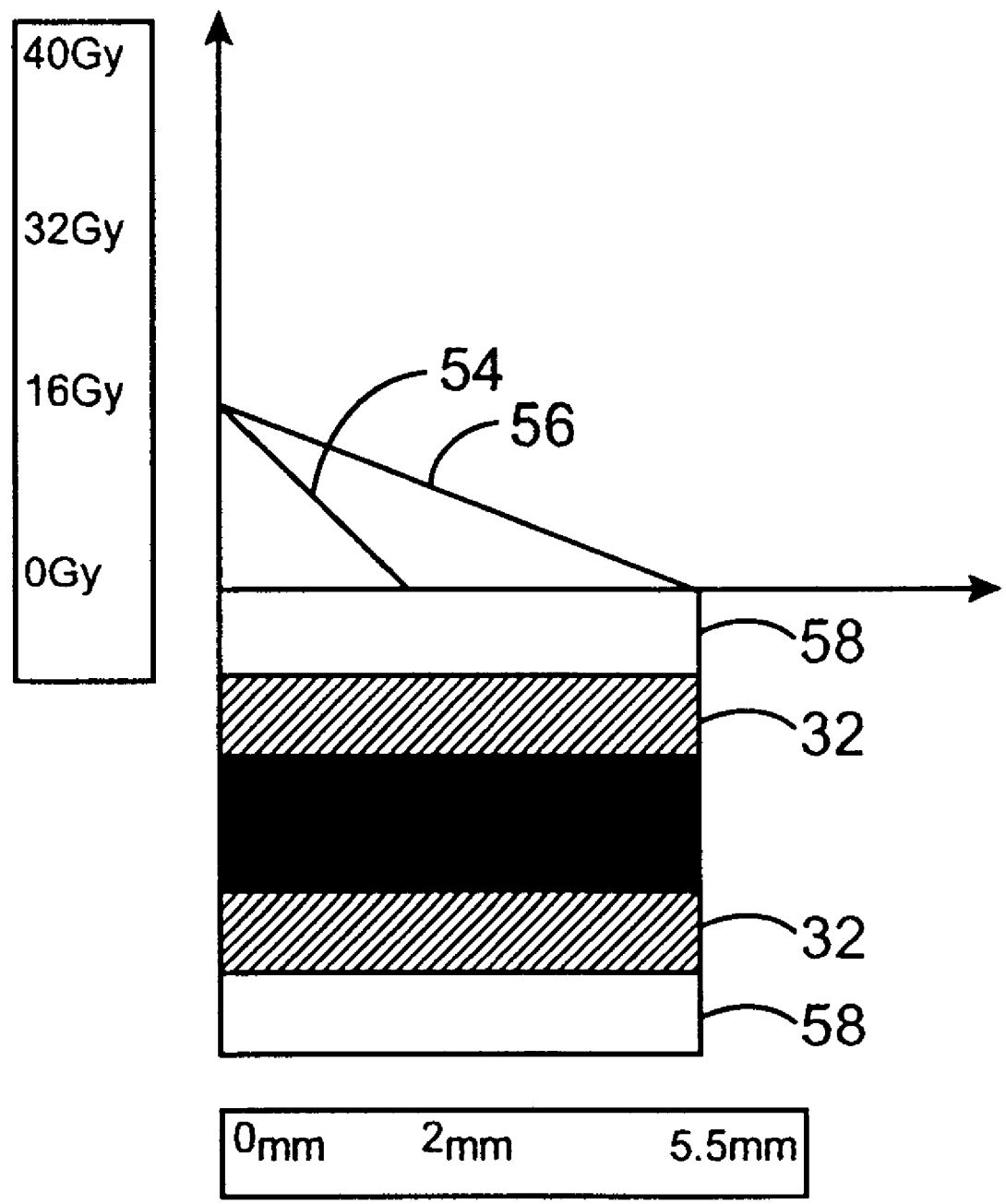
FIG. 8 is a graphical representation of the radiation dose fall off for the apparatus modeled in FIGS. 7A and 7B.

FIG. 8 is a graphical representation of radiation dose fall off at a blood vessel cross section taken at a segment distal to the distal margin of the apparatuses modeled in FIGS. 7A and 7B respectively. Line 54 shows that the radiation dose fall off, from 16 Gy to 0 Gy, effects smooth muscle cells 58 for about 2 mm from the distal end of the distal margin with the radiation shields of FIG. 7A. Line 56 however shows that the radiation dose fall off effect for the device of FIG. 7B on smooth muscle cells 58 is increased to a distance of approximately 5.5 mm from the distal end of the distal margin. Thus, minimization of radiation dose fall off at the distal and proximal ends of a treatment region is greatly improved with the assistance of radiation shields.

Figure 9:
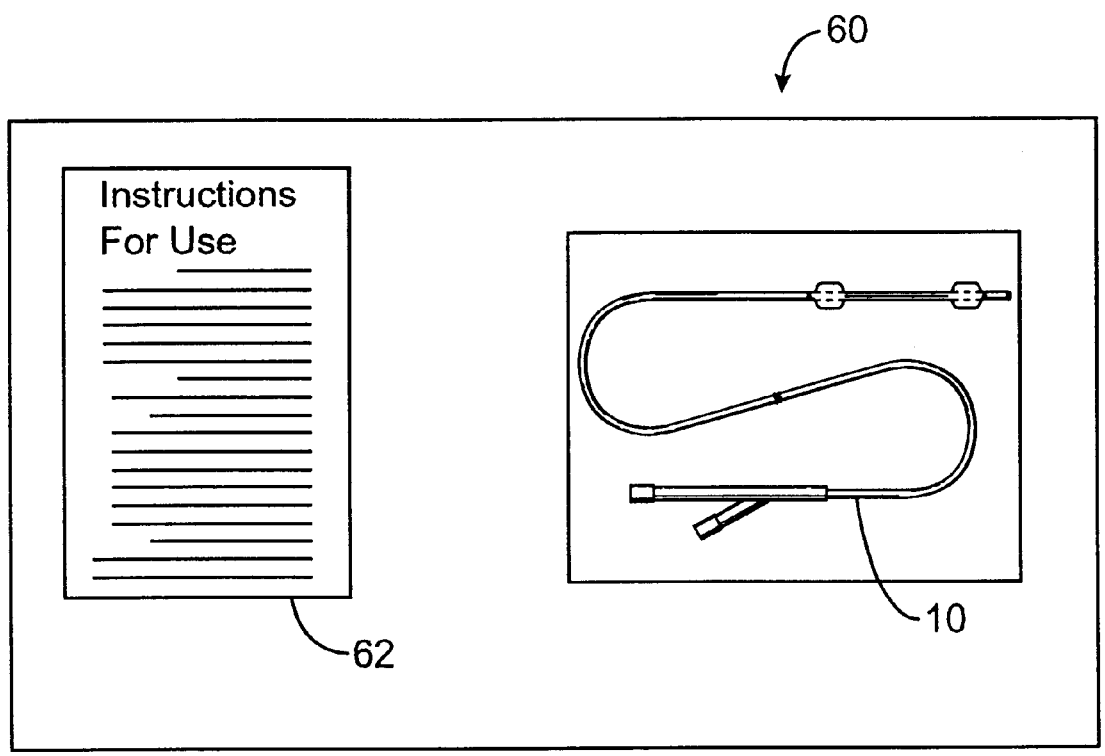
FIG. 9 illustrates a radiation delivery kit including the apparatus of FIG. 4B and instructions for its use.

FIG. 9 schematically illustrates a kit 60 including radiation delivery catheter 10 of FIG. 4B and its instructions for use 62. Radiation delivery catheter 10 may be replaced by any of the catheter structures described herein, while instructions for use 62 will generally recite the step for performing one or more of the described methods. The instruction will often be printed, optionally being at least in-part disposed on the packaging. The instructions may alternatively comprise a videotape, a CD-ROM or other machine readable code, a graphical representation, or the like showing the above methods.

In general, it will be possible to combine the elements of the differing catheters and treatment methods described above. For example, a catheter having an x-ray radiation source as illustrated in FIG. 4B may be fixed relative to the catheter body as illustrated in FIG. 5B. Additionally, the radiation delivery catheter and methods of the present invention may be part of a combination catheter that combines balloon angioplasty and/or other interventional treatments, like stent placement for controlling restenosis, with the presently claimed radiation catheter.

Although certain preferred embodiments and methods have been disclosed herein, it will be apparent from the foregoing disclosure to those skilled in the art that variations and modifications of such embodiments and methods may be made without departing from the true spirit and scope of the invention. Therefore, the above description should not be taken as limiting the scope of the invention which is defined by the appended claims.

What is claimed is:

1. A radiation delivery catheter comprising:
   a catheter body having a proximal end and a distal end;
   a pair of axially spaced apart radiation shields on the catheter body; and
   a radiation source which applies a radiation dose which is substantially uniform in a radial direction over an entire distance between the axially spaced apart shields.

2. A radiation delivery catheter as in claim 1, wherein said radiation shields are permanently affixed to an outer surface of the catheter body.

3. A radiation delivery catheter as in claim 1, wherein said radiation shields comprise elastomeric balloons.

4. A radiation delivery catheter as in claim 3, wherein said elastomeric balloons are inflatable with radiopaque fluid so as to inhibit radiation from reaching tissue beyond the shields.

5. A radiation delivery catheter as in claim 3, wherein said elastomeric balloons have generally flattened end shapes.

6. A radiation delivery catheter as in claim 3, further comprising threading on outer surfaces of said elastomeric balloons.

7. A radiation delivery catheter as in claim 6, wherein the threading has a spiral, helical, or angled pattern.

8. A radiation delivery catheter as in claim 1, wherein said radiation shields are positioned immediately adjacent to the radiation source as to sufficiently minimize radiation dose fall off at distal and proximal ends of a treatment region.

9. A radiation delivery catheter as in claim 1, wherein said radiation source is an x-ray tube.

10. A radiation delivery catheter as in claim 1, wherein said radiation source is a radioisotope.

11. A radiation delivery catheter as in claim 1, wherein said radiation source is a receptacle in the catheter body for receiving radioisotopic materials.

12. A radiation delivery catheter as in claim 1, wherein said radiation source is fixed to the catheter body.

13. A radiation delivery catheter as in claim 1, wherein said radiation source is translated axially relative to the catheter so that the radiation source can travel between the shields to apply the uniform radiation dose.

14. A radiation delivery catheter as in claim 1, further comprising an infusion or aspiration lumen between the shields.

15. A method for applying a radiation dose to a body lumen, said method comprising:
   positioning a first radiation shield at a first location in the body lumen;
   positioning a second radiation shield at a second location spaced apart from the first location in the body lumen; and
   applying a radially uniform radiation dose between the first and second shields;
   wherein the radiation dose directed at tissue outside of the shields is attenuated sufficiently to inhibit hyperplansia outside of the shields.

16. A method as in claim 15, wherein the body lumen is a blood vessel.

17. A method as in claim 15, wherein the first and second radiation shields are positioned on opposite sides of a region at risk of hyperplansia.

18. A method as in claim 15, wherein the first and second radiation shields are positioned between a stented region in a blood vessel.

19. A method as in claim 15, further comprising centering a radiation source within the body lumen with the first and second radiation shields.

20. A method as in claim 15, wherein the first and second radiation shields are balloons inflated with radiopaque fluid.

21. A method as in claim 15, wherein the first and second radiation shields are positioned immediately adjacent to a fixed radiation source so as to inhibit hyperplansia effects at distal and proximal ends of a treatment region.

22. A method as in claim 15, wherein a movable radiation source is translated between the first and second shields.

23. A method as in claim 21 or 22, wherein the applying a radially uniform radiation comprises energizing an x-ray tube.

24. A method as in claim 21 or 22, wherein the applying a radially uniform radiation comprises positioning a radioisotope between the first and second shields, the radioisotope being introduced into a receptacle after the first and second shields are positioned within the body lumen.

25. A method as in claim 15, wherein applying a radially uniform radiation comprises applying a total radiation dose in the range from about 1 Gy to 40 Gy.

* * * * *